United States Patent [19]

Della Sala

[11] Patent Number: 4,650,485

[45] Date of Patent: Mar. 17, 1987

[54] TOTAL ARTIFICIAL HEART

[76] Inventor: Berardino Della Sala, Via Ticino 1, 21021 Angera (Varese), Italy

[21] Appl. No.: 684,015

[22] Filed: Dec. 20, 1984

[30] Foreign Application Priority Data

Dec. 30, 1983 [IT] Italy ................. 24460 A/83

[51] Int. Cl.⁴ ............................................. A61F 2/22
[52] U.S. Cl. .................................................... 623/3
[58] Field of Search .................. 3/1.7; 417/322; 128/1 R

[56] References Cited

U.S. PATENT DOCUMENTS

| 3,182,335 | 5/1965 | Bolie | 3/1.7 |
| 3,511,583 | 9/1968 | Brown | 3/1.7 X |
| 3,733,616 | 5/1973 | Willis, Jr. | 623/3 |
| 3,768,931 | 10/1973 | Willis, Jr. | 417/322 |
| 3,874,002 | 4/1975 | Kurpanek | 623/3 |

Primary Examiner—Richard J. Apley
Assistant Examiner—Alan W. Cannon
Attorney, Agent, or Firm—Henry Sternberg; Bert J. Lewen

[57] ABSTRACT

A total artifical heart prosthesis having a body defining a right ventricle chamber and a left ventricle chamber each provided with an inlet valve and outlet valve, as well as with a flexible membrane dividing each ventricle chamber into a blood-receiving compartment or ventricle proper, and a cardiac function control compartment, in which artificial heart said membranes are urged by a ferromagnetic fluid. Arranged to cooperate with the membranes are electric windings which create magnetic fields producing a sought displacement of the membrane-urging ferromagnetic fluid, i.e. of the membranes themselves. A means is provided for driving the membranes as desired and for powering the electric windings in order to generate the magnetic field.

11 Claims, 16 Drawing Figures

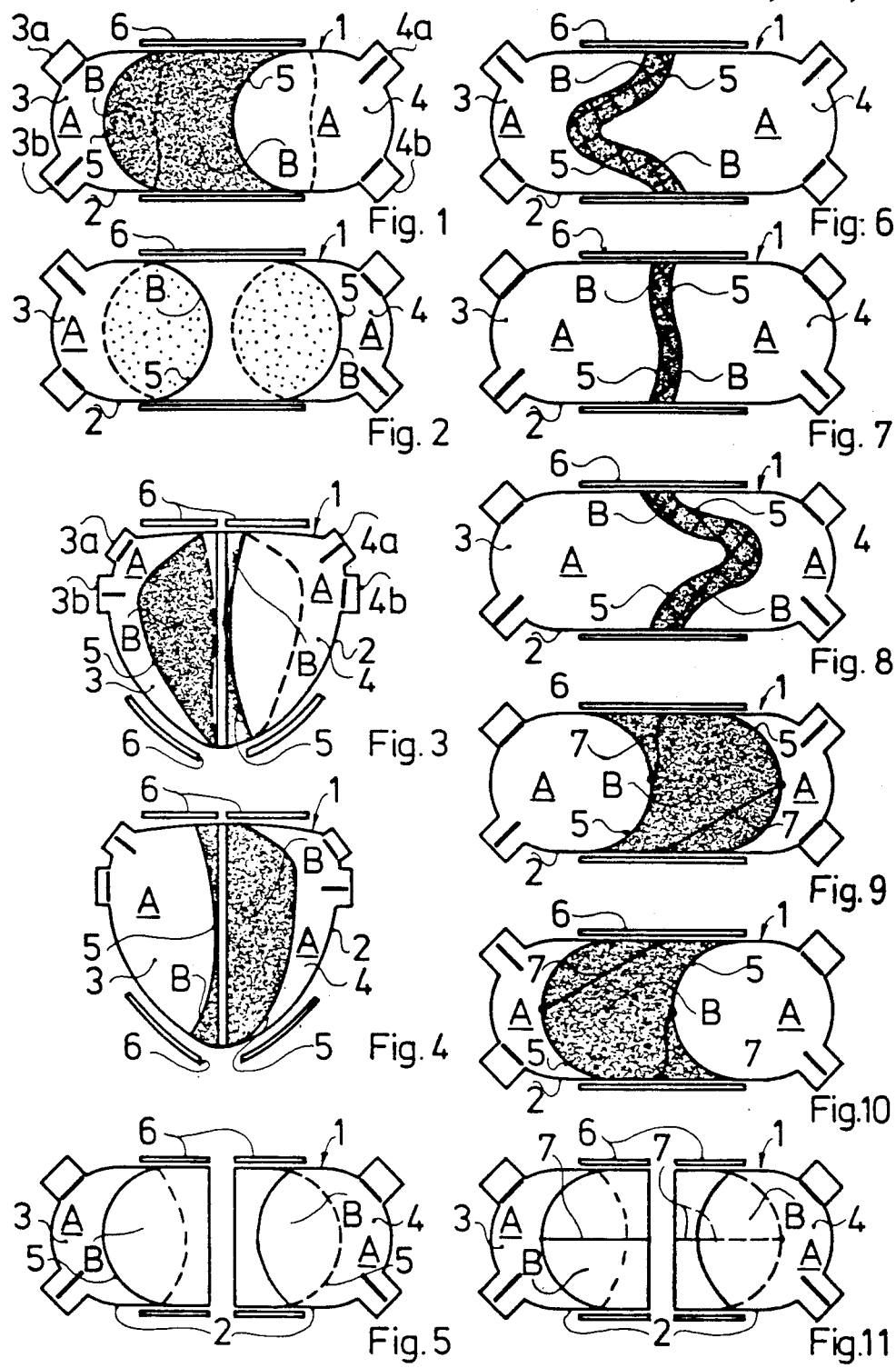

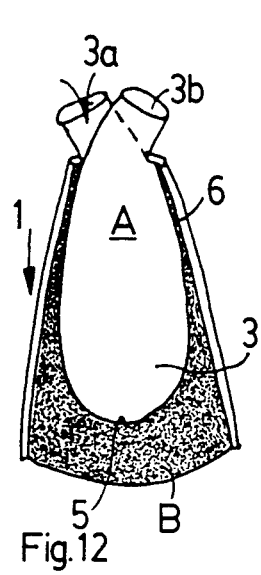
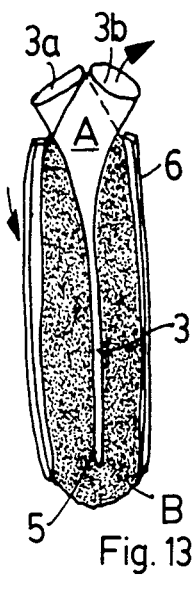
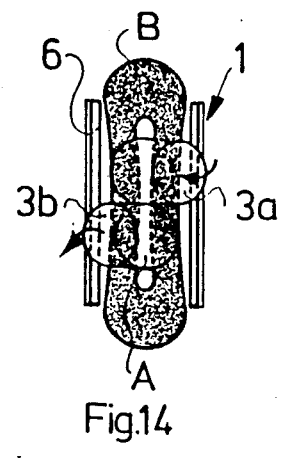
Fig. 12  Fig. 13  Fig. 14
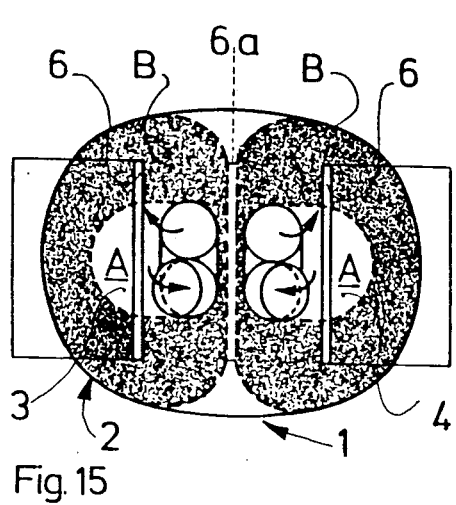
Fig. 15
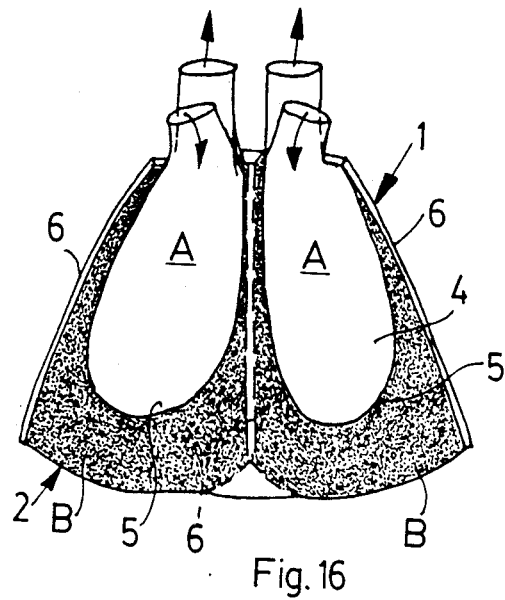
Fig. 16

TOTAL ARTIFICIAL HEART

BACKGROUND OF THE INVENTION

This invention relates to a total artificial heart prosthesis capable of fully replacing a natural heart to perform the cardiac function.

Currently known are various embodiments of total artificial hearts which are formed from biologically inert plastic materials and metals, the same differring in their principles of operation and actuating means employed. Since the first experiments with artificial hearts in 1957, many improvements have been introduced and increasingly more sophisticated approaches have been proposed. The interest in total artificial hearts is also justified by that, contrary to heart transplants which require the availability of such organs and involve well-kown rejection problems, total artificial hearts are suitable for mass production and can, therefore, be made available to a much higher number of patients.

The requisites for an artificial heart prosthesis are: a limited size, on the same order as the human heart; extremely high reliability of operation; prolonged operation capabilities; delivery "flexibility", or capability to supply each time a sufficient delivery to support the entire organism as its demands vary; capability to pump the blood in a gentle manner to avoid hemolysis, i.e. destruction of the red cells; independence of bulky power sources which are difficult to carry around.

The various approaches which are presently known exhibit at least one or more of the main deficiencies listed above, and the need for novel approaches which can obviate them is, therefore, much felt.

In a first artificial heart, blood was pumped by deformation of an elastic membrane, which was driven by compressed air from an external source. That source was fairly bulky and delivery to meet the body demand was complicated to adjust.

A further embodiment employed computer monitoring to control said delivery. Also experimented was a nuclear powered heart, wherein heat was utilized to drive a thermocompressive motor which, through either a pneumatic, or hydraulic, or mechanical system, drove in turn a blood pump. Both attempts enjoyed but limited success, because the devices were complex, bulky, and expensive. It has never been possible to keep laboratory animals alive with them for more than two days.

Additional disadvantages were their liability to mechanical failure, difficulty of insertion with a propensity for obstruction of the venous flow through the right atrium, and excessive hemolysis.

In spite of subsequent improvement with the diaphragm-type pumping element, which improved both the mechanical reliability and hemolysis, extending survival of the laboratory animals up to two weeks, even this embodiment had the disadvantage of forming clots, with attendant internal hemorrhage that could not be checked.

At the present time, the most perfected of artificial hearts is the Jarvik-7 heart, which has polyurethane ventricles supported on aluminum receptacles and tilting disk valves. It succeeded in keeping alive the animals for a period of several months. A calf equipped with such a heart was brought over seven months from a weight of ninety kilograms at the time of the surgical intervention up to above 160 kilograms.

In view of the improvement achieved in the blood handling mechanism, the attention is now focused on improving the power, in particular electric power, converters. Studies are being carried out which are directed toward the realization of an electro-hydraulic power converter having a single moving part and being battery powered. By reversing the direction of rotation of a pump associated with a DC motor, the direction of the hydraulic flow (low-viscosity silicone oil operating a diaphragm similarly to compressed air) is inverted. The hydraulic fluid is pumped back-and-forth between the right and left ventricles, thereby downtime for motion reversal becomes unavoidable.

SUMMARY OF THE INVENTION

It is the aim of this invention to provide a total artificial heart prosthesis which can obviate the shortcomings and deficiencies of presently available artificial hearts.

Based upon an artificial heart prosthesis which comprises at least one ventricle chamber or two ventricle chambers, namely a right ventricle chamber and left ventricle chamber with respective flexible membranes subdividing each ventricle chamber into a blood-receiving compartment and cardiac function control compartment, the indicated aim is achieved, in accordance with the invention teachings, by that the membranes in the ventricle chambers define compartments containing a ferromagnetic fluid, that associated with said compartments are electric windings effective to generate variable magnetic fields causing a controlled displacement of the ferromagnetic fluid in cooperation with said membranes, and accordingly of the membranes themselves, a means of driving the magnetic fields, or the membranes, and that a means of powering the magnetic field generating electric windings is also provided.

The invention utilizes, therefore, the inherent properties of ferromagnetic fluids to produce a desired displacement of the membranes. Said membranes have the advantage that they are readily controlled by means of magnetic fields which are easy to set up and control, while being highly reliable in operation. A further advantage is that the proposed actuation arrangement requires no moving mechanical parts, or mutually cooperating parts, thereby ensuring optimum reliability in operation and durability. Another advantage is afforded by the extremely reduced volume which may be achieved with the proposed solution, thereby the artificial heart prostheses it provides may be readily implanted within a human body. Still another advantage comes from an extremely small power consumption, free of stray paths, so that a prolonged operating range can be achieved. A further advantage comes from the proposed electromagnetic control being independent of any source of compressed air, as usually required heretofore, thus ensuring maximum mobility and freedom for the patient.

According to the invention, moreover, the proposed heart may include an elastic means which would be stretched during the systole phase, so that the same can aid in the membrane return movement during the following diastole phase.

Yet another advantage of the proposed solution is the ease of control of the membranes through electric windings, with suitably different strength and a synchronization which can be achieved in a simple and reliable manner.

A not unimportant advantage of the proposed solution resides in the positive and reliable behavior of the ferromagnetic fluid, said fluids comprising colloids which are currently being extensively investigated and generally utilized in the mechanical industry for sealing applications.

BRIEF DESCRIPTION OF THE DRAWINGS

Further features, advantages, and details of the total artificial heart according to the invention will be more readily apparent from the following description, with reference to the accompanying drawing illustrating some exemplary, and not limitative, embodiments thereof, and where:

FIG. 1 shows a first embodiment of a total heart prosthesis according to the invention, in longitudinal section, with elastic membranes in a final working position thereof, the membranes also appearing in phantom lines at an intermediate position thereof;

FIG. 2 is a sectional view similar to FIG. 1, but showing the membranes in their other final working position, the displacement areas, or volumes, of the membranes being shown at the dotted areas;

FIGS. 3 and 4 show a first modified embodiment;

FIG. 5 shows a further modified embodiment;

FIGS. 6, 7, and 8 show a further modified embodiment of the total heart according to the invention;

FIGS. 9 and 10 show a further modified embodiment including auxiliary and return elastic membranes, the elastic membranes being shown in FIG. 9 in the one final working position and in FIG. 10 in the other final working position;

FIG. 11 shows another modified embodiment of a total heart with elastic membranes; and FIGS. 12-16 show two further modified embodiments.

DESCRIPTION OF THE PREFERRED EMBODIMENTS

With reference first to the diagramatic views of FIGS. 1-11 of the drawing, a total heart according to the invention is generally indicated at 1. The same includes a case or hollow body 2, wherein a right ventricle chamber 3 and left ventricle chamber 4 are formed, the same being respectively provided with inlet valves 3a,4a and outlet valves 3b,4b. Provided on the inside of each chamber 3,4 is a flexible membrane 5 which subdivides its respective chamber 3,4 into a blood-receiving compartment A, or ventricle proper, and a cardiac function control compartment B.

According to the invention, it is now proposed of displacing said membranes by utilizing the properties of a ferromagnetic fluid accommodated in the control compartment B. In FIGS. 1 and 2, the two compartments B are shown in mutual communication, thereby a large volume of ferromagnetic fluid will be contained in the space between the membranes 5. The same applies to the embodiment of FIGS. 9 and 10. In FIGS. 6, 7, and 8 the compartments B are still shown in communication with each other but the volumes of the associated compartments B is here substantially reduced. Correspondingly reduced is also the volume of the ferromagnetic fluid. Further, in order to maintain the mutual positioning of the membranes 5, the same are interconnected in a bonding fashion, e.g. by means of a mesh formation only schematically shown. To displace the membranes 5 from one final working position thereof to the other, i.e. to perform the diastole and systole phases, a means is provided which is operative to vary the magnetic field wherein the ferromagnetic fluid enclosed between said membranes 5 is immersed, advantageously in the form of one or more electric windings schematically indicated at 6. Such windings would be connected to a power supply, or battery, not shown, and associated with a control means, also not shown but being advantageously of the kind of a microprocessor, to perform a respective desired cardiac function, or changes in the same according to varying physical demands from the patient, which changes may be displayed in any convenient forms, such as electric, chemical, chemical/physical, or otherwise. Since, both as regards the power supply and drive means, any of a number of configurations foreign to the inventive concept may be used, no further discussion thereof will be provided herein below.

In the embodiments of FIGS. 3,4 and 5,11, the compartments B accommodating the ferromagnetic fluid are provided separately from each other.

In FIGS. 1 and 2, the pumping action of the membranes 5 takes place alternately in either of the ventricle chambers 3 and 4. Shown in FIG. 6 is the position of the membranes 5 during the systole phase of the left ventricle 3, and in FIG. 7 the membranes occupy a position of diastole phase with respect to the left ventricle 3 while it has already commenced the systole phase for the right ventricle 4, which is then completed in the position shown in FIG. 8.

FIGS. 9 and 10, auxiliary return elastic membranes are indicated at 7 each of which is alternately put under tensile stress during the displacements of the membranes 5 in either directions of movement of the membranes, said auxiliary membranes 7 facilitating repositioning of the membranes 5 on account of their exerting on the same their elastic bias force. The same principle may be applied to a heart in two separate parts, as outlined in FIG. 11. The auxiliary membranes 7 are apertured (not illustrated) to freely admit blood therethrough as they are displaced. FIG. 5 also shows a heart in two discrete parts using the common principle of this invention which underlies all of its embodiments discussed above, i.e. flexible membranes 5 bordering a side wall of the ventricle compartments A.

The embodiments discussed so far may be further modified, in turn, as desired both in respect of their external configurations, and of the size and position of the flexible membranes 5 urged by a ferromagnetic fluid. The latter, albeit known per se, substantially comprises a colloid wherein minute ferromagnetic particles are suspended in a liquid carrier. Moreover, it does not solidify in the presence of a magnetic field; it is magnetized but left liquid. Within the same, when subjected to a magnetic field, there is developed a volume force which is used, according to the invention, to cause displacement of said ferromagnetic fluid, and hence of the membrane(s) containing it. A further advantage of the proposed ferromagnetic fluids is that the same exhibit neither electric currents nor charges. Its use is, therefore, free of any secondary effects on the patient.

The invention is directed, accordingly, to a power converter of novel design which may be likened to an electromagnetic motor, which allows the aim underlying this invention to be effectively achieved and affords the advantages outlined in the introductory part. In particular, moving mechanical parts are eliminated, greatly reduced volumes can be obtained, hemolysis is prevented, and complete freedom from connection to disadvantageous sources of compressed air is ensured such as have heretofore provided best performance.

Furthermore, the patient is quite self-sufficient, thanks to the possibility of using small size batteries. A particular advantage of the proposed solution is that with the newly proposed ferromagnetic fluid electromagnetic motor converter any requirement of the actual cardiac cycle can be successfully met, i.e. taking into account the notoriously different power and pressure requirements for the right and left ventricles, by merely manipulating the means of driving the variable magnetic fields required. In practice, it would be possible to introduce any modifications or changes both in respect of the configurations of the elastic membranes and the outer construction, without departing from the scope and spirit of the instant invention.

It is also contemplated by the invention concept that the relative positions of the ventricle compartments A and compartments B accommodating the ferromagnetic fluid may be exchanged, as shown diagrammatically in FIGS. 12-16. According to this solution, the ventricle-forming compartment A would be provided within an outer compartment B accommodating the ferromagnetic fluid, associated with said compartments B there being the electric windings 6 for generating the variable magnetic field. This solution retains the advantages of the compact feature, i.e. of a comparable size to that of a human heart, as already pointed out herein above in connection with the other embodiments.

The sectional views of FIGS. 12 and 13 illustrate the diastole and systole positions of the ventricle A, respectively, FIG. 14 being a top view of the single ventricle embodiment of FIGS. 12 and 13. FIGS. 15 and 16 show a two-ventricle heart and a middle winding 6a. The latter enables, in cooperation with the outer windings 6, induction of different strength magnetic fields in the two ventricle compartments A, and accordingly, different pressures to be established therein, e.g. the one being approximately one third of the other, just as is to be found in the human heart.

. As brought out in the drawing, the ventricle compartments A have a substantially elongate shape bag-fashion, and the outer control compartments B containing the ferromagnetic fluid encircle the ventricle compartments A substantially continuously along their height and at the lower end.

From the foregoing description it may be readily noted that the proposed structure may be likened in practice to a membrane electromagnetic pump. This falls as such within the scope of this invention, and as preferential applications therefor mention is made, as an example, of such applications as the transferment or transport of sensitive liquids, such as wine, milk, and drinks in general, as well as of inflammable liquids or gases—since no moving mechanical parts are present—fluids in unstable mixture forms, and so forth.

All of the features which may be inferred from the specification, claims, and drawing are to be regarded as substantial to this invention, both individually and in any combination thereof, wherever within the purview of the invention.

I claim:

1. A total artificial prosthesis comprising at least one ventricle-like blood-receiving compartment having inlet and outlet valve means for receiving and discharging the blood, at least one wall of said compartment being a flexible membrane,
   a fluid receiving compartment on the opposite side of said membrane and separated from said blood receiving compartment by said flexible membrane,
   a quantity of ferromagnetic fluid substantially filling said second compartment,
   electro magnetic means cooperating with said second compartment, said electro magentic means being operative to generate a variable magnetic field causing a desired displacement of the ferromagnetic fluid and in response thereto a desired displacement of said membrane with respect to said blood receiving compartment, and
   control means for controlling the action of said electro magnetic means and thus of said membrane.

2. A total artificial heart prosthesis comprising:
   at least one ventricle-like blood-receiving internal bag having laterally opposed side portions and a bottom portion formed of a flexible membrane and having inlet and outlet valve means for receiving and discharging the blood from and to, respectively, the interior of said internal bag,
   an external bag having laterally opposed side portions and a bottom portion formed of a flexible membrane substantially surrounding said side and bottom portions, respectively, of said at least one blood-receiving internal bag and forming a closed external fluid receiving compartment between said internal and external bags,
   a quantity of ferromagnetic fluid substantially filling said closed external fluid receiving compartment,
   a pair of electromagnet means cooperating respectively with said opposed side portions of said external bag for movement therewith and for generating a magnetic field therebetween for causing displacement of a portion of said ferromagnetic fluid within said external compartment from a location in the bottom of said external compartment to locations in said external compartment between the corresponding lateral side portions of said external and said internal bags for moving said laterally opposed side portions of said external bag and thus said pair of electromagnet means, toward each other,
   whereby the magnetic force generated between said pair of electomagnet means increases as the distance therebetween decreases so as to facilitate substantially complete and substantially rapid collapse of said internal bag in response to actuation of said magnet means.

3. A total artificial heart prosthesis according to claim 2, comprising sheet-like wall means supported on said opposed side portions of said external bag for swingable movement from a first condition in which the lower end portions of said wall means are spaced father apart than the upper end portions, said upper end portions being in proximity to said valve means, to a second condition in which said lower end portions are closer to each other than in said first condition thereof, said electromagnet means being in the form of electric coils incorporated in said sheet-like wall means.

4. A total artificial heart prosthesis according to claim 2, in which said electromagnet means comprises electric coils for generating the magnetic field, said coils being contained in said side portions of said external bag.

5. A total artificial heart prosthesis according to claim 2, comprising a second ventricle-like blood receiving internal bag, in side-by-side relation to said first mentioned internal bag, said second internal bag formed of a flexible membrane and having inlet and outlet valve means for receiving and discharging the blood from and to, respectively, the interior of said second internal bag, and a second external bag substantially surrounding said second internal bag and forming a second closed external fluid receiving compartment between said second internal and said second external bag, said second external bag formed of a flexible membrane, a second quantity of ferromagnetic fluid substantially filling said second closed external compartment, a second pair of electromagnet means cooperating with the laterally opposed side portions of said second external bag and adapted to generate a second magnetic field for causing displacement of portions of said second quantity of ferromagnetic fluid within said second external compartment between a first condition in which a given portion of said ferromagnetic fluid is in the spaces between adjacent side portions of said internal and external bags, and a second condition in which a substantially larger amount than said given amount of ferromagnetic fluid is in said spaces between said side portions for substantially collapsing said second ventricle-like blood receiving internal bag and moving said second pair of electromagnet means toward one another, whereby the magnetic forces generated therebetween increase as the distance therebetween decreases so as to facilitate substantially complete and substantially rapid collapse of said second internal bag in response to actuation of said second pair of electromagnet means.

6. An artificial heart prosthesis according to claim 5, characterized in that said electric windings, i.e. the magnetizing currents therethrough, are dimensioned to produce different power, or flow rate, levels in said two ventricle chambers, similarly to the power ratio to be found in the ventricle chambers of a human heart.

7. An artificial heart prosthesis according to claims 5, wherein said ventricle chambers have an elongate bag-like shape.

8. An artificial heart prosthesis according to claims 5, characterized in that the outer compartments containing said ferromagnetic fluid are arranged to encircle said ventricle compartments substantially continuously over their heights and lower ends along the sides thereof.

9. A total artificial heart prosthesis according to claim 5, in which one of each of said first and second pair of electromagnet means is located intermediate said first and second ventricle-like blood-receiving internal bags.

10. A total artificial heart prosthesis according to claim 9, further comprising a pair of outer movable sheet-like wall members exteriorly of said side wall portion of said first and second external bags, respectively, the other of each said pair of electromagnet means being supported on said outer sheet-like wall members for generally pivotable movement therewith whereby the lower end portions of said sheet-like wall members pivot toward and away from each other in response to actuation or deactuation, respectively, of said electromagnet means.

11. In an artificial heart prosthesis:
an inner flexible bag having inlet and outlet openings and defining a blood receiving and dispensing chamber,
an outer flexible bag having bottom and side portions surrounding bottom and side portions of said inner bag and forming a closed outer chamber between said inner bag and said outer bag,
ferromagnetic fluid filling said closed outer chamber,
a pair of opposed electromagnetic means for generating a magnetic field therebetween for displacing the ferromagnetic fluid in said closed compartment from a first condition in which a given portion thereof is in the bottom portion of said closed outer chamber and the remaining portion thereof is in the upper portions of said outer chamber between adjacent side portions of said inner and outer flexible bags, to a second condition in which a greater portion of said fluid is in said upper portions of said outer chamber for applying pressure on said inner flexible bag therebetween for dispensing the blood therefrom, in response to which said opposed side portions of said outer bag and thereby said electromagnet means move toward each other, said electromagnetic means cooperating with said side portions of said outer bag for movement therewith, whereby the magnetic force on said ferromagnetic fluid increases in response to such movement of said electromagnet means toward each other so as to facilitate more complete collapse of said inner bag.

* * * * *